United States Patent [19]

Wieland et al.

[11] 4,276,769
[45] Jul. 7, 1981

[54] APPARATUS FOR DETERMINING THE CARBON DIOXIDE CONTENT OF A LIQUID, ESPECIALLY A BEVERAGE

[76] Inventors: Dieter Wieland, Oststrasse 1, 4000 Düsseldorf; Hartnut Meinert, Hünnefeldstrasse 22, 4950 Minden/Westfalen, both of Fed. Rep. of Germany

[21] Appl. No.: 93,709

[22] Filed: Nov. 13, 1979

[30] Foreign Application Priority Data

Nov. 14, 1978 [DE] Fed. Rep. of Germany ....... 2849401
May 16, 1979 [DE] Fed. Rep. of Germany ....... 2919767
May 18, 1979 [DE] Fed. Rep. of Germany ....... 2920154

[51] Int. Cl.³ .............................................. G01N 7/14
[52] U.S. Cl. .......................................... 73/19; 73/64.2
[58] Field of Search ........................ 73/19, 61 R, 64.2

[56] References Cited

U.S. PATENT DOCUMENTS 2,736,190   2/1956   Bockelmann et al. ................... 73/19
3,673,853   7/1972   Griswold et al. ........................ 73/19

*Primary Examiner*—Herbert Goldstein
*Attorney, Agent, or Firm*—Sprung, Felfe, Horn, Lynch & Kramer

[57] ABSTRACT

An apparatus for measuring the carbon dioxide content of fluids, especially beer, is described in which there are two pistons disposed on either side of an expansion chamber, the pistons being in cylinders of different displacement volumes, the pistons being displaceable axially together to effect expansion whereby equilibrium between carbon dioxide in gas and in fluid is established thereby permitting, via pressure measurements, a determination of the carbon dioxide content of a fluid sample.

17 Claims, 5 Drawing Figures

4,276,769

APPARATUS FOR DETERMINING THE CARBON DIOXIDE CONTENT OF A LIQUID, ESPECIALLY A BEVERAGE

BACKGROUND

The subject matter of the invention is an apparatus for determining the carbon dioxide content of a liquid, especially of a beverage.

It is known to determine the carbon dioxide content of a beverage, such as beer for example, with an apparatus in which an expansion chamber is provided in a housing for receiving the liquid to be measured. This expansion chamber, however, is connected to a liquid inlet-outlet by an inlet-outlet conduit provided with a valve means. It furthermore contains a pressure gauge as well as a temperature gauge, and its volume is variable according to the position of a piston displaceably disposed in it. The apparatus furthermore has a handle whereby the piston can be drawn from a first position in which the volume of the expansion chamber is at a minimum, to a second position in which the volume of the expansion chamber is at a maximum.

The basis of the known apparatus is the fact that, when there is a state of equilibrium between the carbon dioxide content of the liquid contained in the expansion chamber and the carbon dioxide content of a space situated above the liquid, the carbon dioxide gas pressure which establishes itself in this chamber is an index of the carbon dioxide content of the liquid, depending on the temperature of the liquid.

The measuring process is performed in the known apparatus as follows:

The expansion chamber is completely filled through the feed conduit with the liquid to be measured. Then it is closed by the use of the valve means and the piston is drawn by the handle to the second position, such that a carbon dioxide gas-filled chamber forms above the liquid. The establishment of the equilibrium is assisted and accelerated by shaking the apparatus by hand. The pressure that establishes itself is read on the pressure gauge and, on the basis of the temperature, the corresponding carbon dioxide content of the liquid can be calculated or read from tables in a known manner.

The known apparatus has the disadvantage that it is difficult to operate. Several valves or cocks have to be opened by hand and closed again, the piston has to be drawn out by hand, and the apparatus has to be shaken by hand.

Apparatus have also become known in which the establishment of the state of equilibrium is achieved by special mechanical devices (vibration) or electrical devices (electrolysis).

But these apparatus are relatively complicated in operation. Practice has shown that the known apparatus also require relatively large amounts of test liquid, are liable to trouble, and give readings which are not always repeatable.

Furthermore, an apparatus is known for the continuous determination of the carbon dioxide content of a liquid flowing through a conduit (DE-OS No. 2,634,971), in which a partial stream of the liquid is carried by a measuring conduit through a measuring cell in which an outgassing of the liquid constantly takes place, a static liquid pressure measuring means being provided ahead of the measuring cell and a device for measuring the temperature and a device for measuring the outgassing pressure being disposed within the measuring cell. These measuring apparatus emit electrical signals which are continuously delivered to an electronic computer for evaluation and read-out. The outgassing of the liquid is assisted by constructing the inner chamber of the measuring cell as a cylinder, at least in the area of the entrance of the liquid, and the measuring conduit discharges tangentially to the circumferential surface of the cylinder and the discharge of the liquid takes place in the direction of the axis of the cylinder. At or immediately ahead of the entrance aperture the measuring cell has a narrowing of cross section for the purpose of achieving a sufficient pressure gradient.

With this known apparatus very accurate and repeatable measurements can be obtained, though the technical expense is relatively high.

THE INVENTION

The invention sets out from the fact that in many cases it is not at all necessary to determine continuously the carbon dioxide content of a liquid, such as beer. Instead, it will often suffice to measure it at certain intervals of time which must be closer together the more accurately the time relationship of the carbon dioxide content is to be determined or the greater the probability is of relatively rapid changes in the carbon dioxide content.

Accordingly, the problem existed of devising an apparatus whereby the carbon dioxide content of a flowing liquid or of a liquid in a container, especially a beverage such as beer, for example, can be determined at given intervals of time. The apparatus should provide accurate and repeatable measurements, and be of very simple construction and easy and reliable to use, so that it will be usable even under severe conditions of operation. It should require only a small amount of liquid for each measurement so as to keep the adjusting time and measuring time brief and avoid any great loss of liquid if the test liquid is not to be returned to the circuit.

The invention sets out from an apparatus for the determination of the carbon dioxide content of a liquid, especially a beverage, having a housing containing an expansion chamber for receiving the liquid to be measured, which chamber is connected by a supply line and a drain line each equipped with a valve means to a liquid inlet and outlet, respectively, and also is connected to a temperature measuring device, and whose volume is variable according to the position of a piston displaceably guided in it, and having a means for the displacement of the piston from a first position in which the volume of the expansion chamber is at a minimum to a second position in which the volume of the expansion chamber is at a maximum.

The solution of the above-described problem is accomplished in accordance with the invention by disposing in hollow cylindrical sections of the inner chamber of the housing two displaceably guided pistons which are in line with one another axially, are rigidly joined to one another, and have different diameters, the expansion chamber being disposed between the confronting end faces of the piston and being joined at its one end to the liquid feed line and at its other end with the liquid drain line, the liquid feed line being carried through the one piston and the liquid drain line through the other piston, and the pistons serving as valve means in that the liquid feed line and the liquid drain line are open in the first position of the pistons, and are closed upon the movement of the pistons to the second position, and the means for the displacement of the piston bringing about a positively controlled automatic displacement of the pistons from the first position to the second position. Various advantageous embodiments of the apparatus of the invention are contemplated.

The apparatus of the invention, for example, can be constructed as a portable apparatus. The apparatus can then easily be carried along on inspection tours, because due to a special configuration it is very easy to carry and handle.

All of the embodiments of the apparatus of the invention can also be permanently installed, for example in a bypass of a liquid line.

It can be desirable to deliver the measurements to a central processing apparatus. In that case, apparatus in accordance with the invention can be disposed within a larger apparatus at a number of important points at which the carbon dioxide content of the liquid is to be determined, and which can be supervised from a central terminal.

It has been found that the expansion chambers can be kept small in the apparatus of the invention, so that it can be operated with relatively small amounts of liquid. The mechanical design of the apparatus is extremely simple, sturdy, and reliable in operation. Operation is very simple, since there is no need for opening and closing valves by hand or for additional shaking of the apparatus, and the pistons do not have to be moved by physical power. The housing can consist at least partially of transparent material so that the interior of the expansion chamber can be observed visually.

BRIEF DESCRIPTION OF DRAWINGS

Examples of the embodiment of the apparatus of the invention will be described with the aid of the appended drawings, wherein.

DESCRIPTION OF SPECIFIC EMBODIMENT

Figure 1:
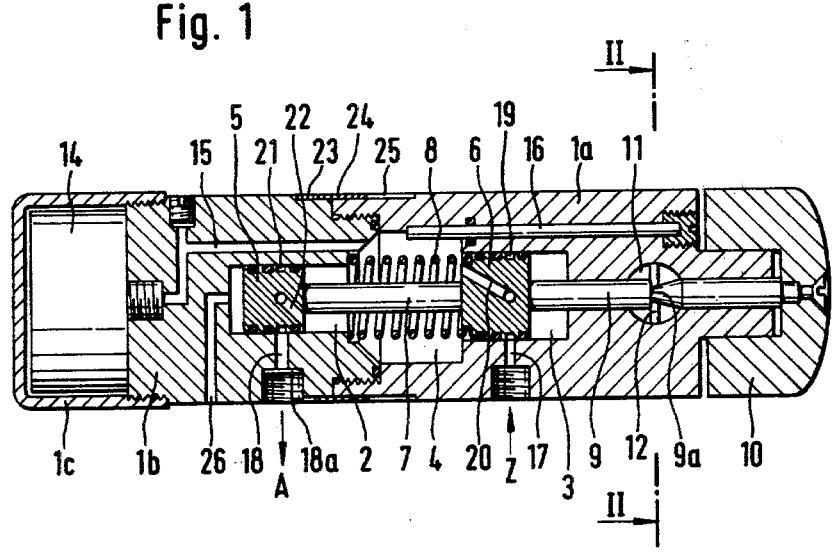
FIG. 1 is a longitudinal cross sectional view taken through a first embodiment of an apparatus for determining the carbon dioxide content of a liquid.
Figure 2:
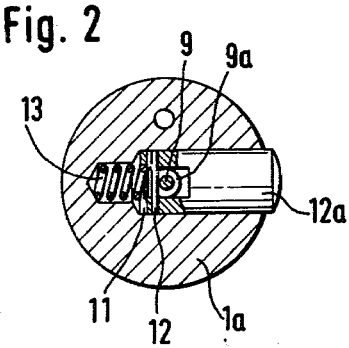
FIG. 2 is a cross section taken along line II—II of FIG. 1.

The embodiment for the determination of the carbon dioxide content of a liquid which is represented in FIGS. 1 and 2 is primarily designed for single measurements or measurements at relatively great intervals of time.

It has a housing consisting of two parts 1a and 1b which can be attached to one another by screw threads. The inner chamber of the housing is, as a whole, of hollow cylindrical construction, and consists of three successive sections, a first, hollow cylindrical section 2 in which a piston 5 is displaceably guided, a second hollow cylindrical section 4 which serves as an expansion chamber in a manner to be explained further below, and a third, hollow cylindrical section 3 in which a piston 6 is displaceably guided. The diameter of the hollow cylindrical section 3 is greater than the diameter of the hollow cylindrical section 2, and the diameter of the piston 6 is greater than the diameter of the piston 5. The diameter of the hollow cylindrical section 4 is inconstant axially and greater overall than the diameter of the hollow cylindrical sections 2 and 3. The piston 5 is rigidly joined by means of a rod 7 extending through the expansion chamber 4 to the piston 6 which is in axial alignment with it. The piston 6 is joined on its side facing away from piston 5 to a rod 9 which passes all the way through the housing 1a. At the outer end of the rod 9 there is disposed a handle 10. In the middle hollow cylindrical section 4 of the housing interior there is disposed a compression spring 8 whose one end thrusts against a shoulder of the housing and whose other end thrusts against the face face of the piston 6. Spring 8 therefore exercises on the piston 6 a force which seeks to push piston 6 and piston 5 connected to it to a position wherein the piston 6 abuts against the end surfaces defining the hollow cylindrical section 3. The displacement is blocked by a releasable catch means. The catch means is disposed in a bore 11 running transversely of the housing axis in part 1a. It has a catch 12 which is displaceable against the force of a spring 13 and which engages a circumferential groove 9a in the rod 9. The catch 12 is connected to a pushbutton 12a extending outwardly. When the pushbutton 12a is pressed, the catch 12 is forced out of the groove 9a and the rod 9 is released, such that the pistons 5 and 6 are displaced by the force of the spring 8.

The middle section 4 of the inner chamber of the housing is connected by a passage 15 to a pressure gauge 14. Furthermore, a portion of a thermometer 16 disposed in housing part 1a extends into it.

The apparatus furthermore has a liquid inlet Z which is connected by a passage 17 to the hollow cylindrical section 3 and a liquid outlet A which is connected by a passage 18 to the hollow cylindrical section 2.

In embodiments in which the liquid outlet A is not connected back to a liquid conduit or a liquid container that is under pressure, a throttling means, e.g., a diaphragm 18a, is disposed in the liquid outlet A.

Furthermore, in the outer periphery of piston 6 which is sealingly guided in the hollow cylindrical section 3 there is disposed a groove 19 which is connected to a passage 20 running through the piston 6 and terminating in the inner chamber of the housing at the end of piston 6 facing the piston 5. Likewise, there is provided at the outer periphery of piston 5 guided sealingly in the hollow cylindrical section 2 a groove 21 which is connected to a passage 22 which runs through the piston 5 and terminates in the inner chamber of the housing at the piston face confronting the piston 6.

The hollow cylindrical section 2 of the inner chamber of the housing is connected at its end by a passage 26 to the exterior.

The pressure gauge disposed at the one end of the housing part 1b is protected by a cap 1c threaded onto the housing.

The operation of the apparatus represented in FIGS. 1 and 2 is as follows:

Pistons 5 and 6 can basically assume two different positions. A first position is represented in FIG. 1. In this position both pistons are displaced leftward in the drawing. In this first position the rod 9 is held by the catch 12, so that a force acting rightwardly in the drawing is exercised by spring 8 but no displacement of the pistons can take place. In this first position the volume of the housing interior, which is composed of the middle hollow cylindrical section 4 and the adjacent portions of the hollow cylindrical sections 2 and 3, is at a minimum. Furthermore, the groove 19 in piston 6 is opposite the inner end of the passage 17, while the groove 21 of piston 5 is opposite the inner end of passage 18. This means that liquid inlet Z and liquid outlet A are open. In this position, when the apparatus is connected to a liquid conduit or a liquid container, the liquid to be measured can enter at Z and passes through passages 17 and 20 into the chamber 4, flows through it and flows through passages 22 and 18 and the liquid outlet A back out of the apparatus. The state of the liquid flowing through the chamber 4 can be observed because the housing part 1a is made of transparent material or has a viewing window disposed in front of the chamber 4. As soon as the space between the confronting end faces of pistons 5 and 6, which hereinafter will be referred to as the expansion chamber 4, is filled and the liquid flows bubble-free, the catch means is released by the pushbutton 12a. The catch 12 releases the rod 9 and the pistons 5 and 6 are abruptly displaced rightwardly in the drawing under the effect of the compression spring 8, until the piston abuts against the end wall of the hollow cylindrical section 3. The liquid inlet Z and the liquid outlet A are thereby closed, on the one hand, and on the other hand the volume of the expansion chamber 4 enlarges until, in the second position of pistons 5 and 6 at the end of the displacement, it has reached a maximum. At the same time a great expansion of the liquid enclosed in the expansion chamber takes place. The release of the carbon dioxide contained in the liquid is accomplished by a very rapidly produced sharp drop in pressure. The liquid flows into the expansion chamber at a pressure above the saturation pressure. If the liquid outlet A is not connected back to a liquid conduit or to a liquid container under pressure, the pressure in the expansion chamber 4 can be substantially sustained by a diaphragm 18a. By the displacement of the piston additional volume is created resulting in a vacuum. An equilibrium then establishes itself between the carbon dioxide content of the liquid and the gas pressure in the liquid-free chamber. The establishment of the equilibrium can be recognized through the viewing window or transparent parts of the housing by the fact that the liquid specimen is "clear", i.e., it no longer contains gas bubbles. Now the pressure can be read on the pressure gauge 14. Furthermore, the temperature of the liquid is determined by means of the thermometer 16. In order to obtain a very reliable temperature reading, the thermometer 16 is arranged such that its probe lies in the expansion chamber 4 immediately adjacent the point of entry of the passage 20 through which the liquid flows into the expansion chamber 4. From the measurements obtained it is then possible to determine the carbon dioxide content of the liquid on the basis of known formulas or by means of tables.

After the measurement is completed, the pistons 5 and 6 are returned to the first position by means of the knob 10 acting on rod 9, and the catch means is engaged by the action of the spring 13 and locks the pistons in this first position. The liquid inlet Z and the liquid outlet A are reopened in this position and the apparatus is ready for a second measurement.

For the rapid determination of the carbon dioxide content without resorting to tables which must be carried with the apparatus, a special device is provided on the outside of the housing 1a and 1b for the rapid determination of the carbon dioxide content. This device has a rotatable ring 24 incorporated into the outer surface of the housing, and having at both its margins an appropriately calibrated scale which is opposite a respective scale on rings 23 and 25 affixed to the housing. By turning the ring 24 it is possible to read directly from the apparatus, for every pressure read from the scale, and for the temperature read from the thermometer, a corresponding value of the carbon dioxide content of the liquid.

The establishment of the state of equilibrium can be assisted and accelerated by providing on the rod 7, within the expansion chamber 4, in a manner not shown, a leaf spring element disposed transversely of the direction of movement and containing a bore disposed in the direction of movement of the piston. Upon the abrupt displacement of the pistons 5 and 6 from the first position to the second position after the release of the catch means, the leaf spring element is set in vibration and the vibrations are communicated to the surrounding liquid thus accelerating by mechanical action the establishment of the state of equilibrium.

The embodiment of the apparatus for determining the carbon dioxide content of a liquid, which is described in FIGS. 1 and 2, is, as stated, especially suitable for the performance of single measurements or measurements at relatively great intervals of time. For this purpose it can be designed as a portable hand instrument, it being especially desirable, when the apparatus is used for determining the carbon content of beer, to select the outside diameter of the apparatus such that it corresponds to the diameter of one of the standard bottles used. The apparatus can then be transported together with bottles in a conventional kit box. Of course, however, the apparatus represented in FIGS. 1 and 2 can also be permanently attached to a liquid tank or liquid pipeline.

As described, the pressure gauge 14 in the embodiment shown in FIGS. 1 and 2 is directly connected by the passage 15 to the expansion chamber 4. Now, it has been found in practice that often a considerable pipeline pressure prevails in the liquid lines, which is greater than the pressure shown by the full deflection of the pointer on the pressure gauge 14. Now, if the pressure gauge is connected to the expansion chamber in all operating states of the apparatus, when the apparatus is connected to a liquid pipeline, the abrupt entry of the liquid into the expansion chamber 4 produces a shock pressure resulting in a full deflection of the pointer of the pressure gauge. In the case of very high line pressures, the pressure gauge can even be damaged. In what follows, a variant of the embodiment of FIGS. 1 and 2 will be described with the aid of FIG. 3, in which the connection between the pressure gauge and the expansion chamber is made only when the pistons are in the position in which the actual measurement is performed, but not in the position wherein the liquid flows into the inner chamber of the apparatus.

Figure 3:
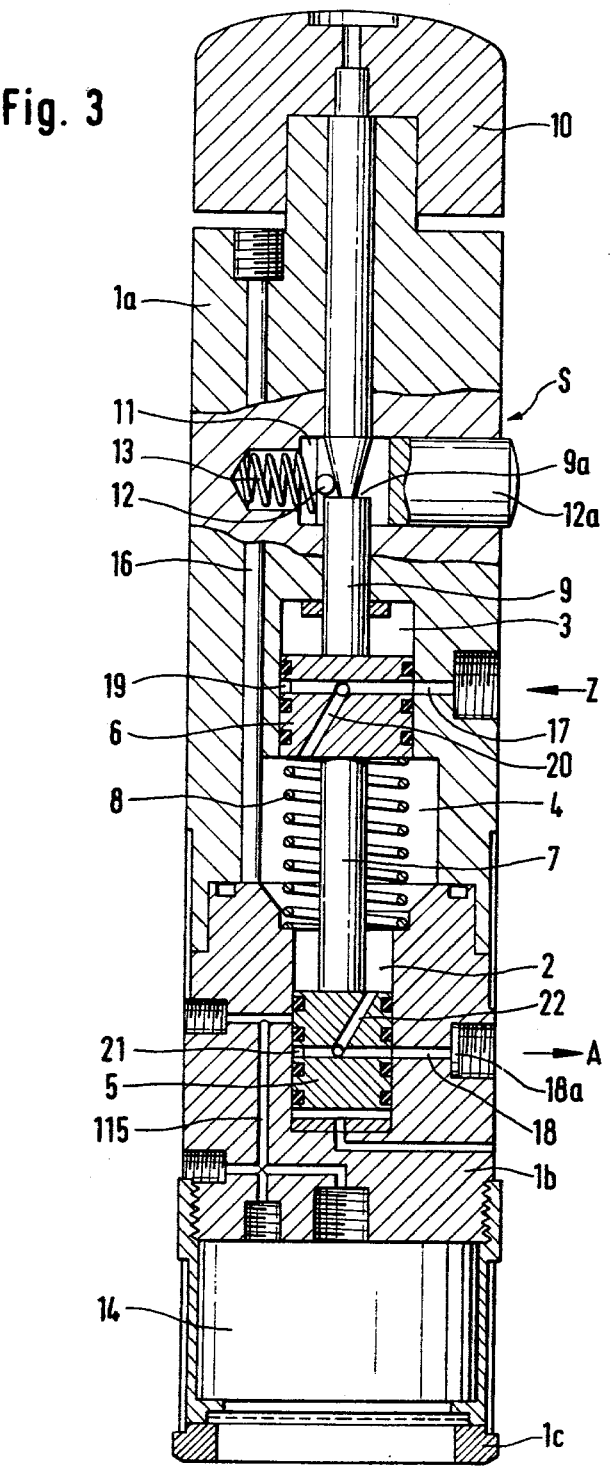
FIG. 3 is a longitudinal cross-sectional view similar to FIG. 1 of a variant of the embodiment shown in FIG. 1.

In FIG. 3, the same numbers are used for parts corresponding to the embodiment represented in FIGS. 1 and 2, and the preceding description may be consulted regarding these parts.

It is furthermore pointed out that FIG. 3 shows a longitudinal cross section through the apparatus wherein the plane of section in the area identified by the letter S is turned 90° from the plane of section in the other areas.

The construction of the embodiment shown in FIG. 3 is substantially the same as that of the embodiment seen in FIGS. 1 and 2. The difference lies in the fact that the pressure gauge 14 is connected by a passage 115 to the hollow cylindrical section 2. The groove 21 in piston 5 is so disposed that, in the first position of piston 5, in which the piston abuts against the surface defining the hollow cylindrical section 2, it is opposite the passage 18 connected with the liquid outlet A. In this position, therefore, the expansion chamber 4 is connected to the liquid outlet A. In the second position of the piston 5, in which the piston 6 abuts against the surface defining the hollow cylindrical section 3, the groove 21 is instead opposite the passage 115 connected to the pressure gauge. This means that in this position the pressure gauge 14 is connected to the expansion chamber 4 through the passage 115, the groove 21 and the passage 22.

The pressure gauge 14 disposed on the end of the housing part 1b is protected by a cover 1c threaded onto the housing.

The operation of this embodiment is as follows:

In the above-mentioned first position, which is represented in FIG. 3, the two pistons 5 and 6 are displaced downwardly in the drawing. In this first position the rod 9 is locked by a ring 12, so that the compression spring 8 exerts a force directed upwardly in the drawing, although no displacement of the piston can take place. In this position the volume of the inner chamber of the housing is at a minimum. Furthermore, the groove 19 in the piston 6 is opposite the outlet end of passage 17, while the groove 21 of the piston is opposite the outlet end of passage 18. This means that liquid inlet Z and liquid outlet A are open. In this position, in the case of an apparatus connected to a liquid line or to a liquid container, the liquid to be measured can enter at Z and it will pass through the passages 17 and 20 into the chamber 4, flow through it, and flow back out of the apparatus through passages 22 and 18 and the liquid outlet A. The line pressure that develops, however, cannot act through the passage 115 on the pressure gauge 14. The state of the liquid flowing through the chamber 4 can be observed since the housing part 1a is made of transparent material or has an inspection glass disposed in front of chamber 4. As soon as the expansion chamber disposed between the confronting faces of pistons 5 and 6 is filled with liquid and the liquid flows bubble-free, the catch means is released by pressing the pushbutton 12a. The catch 12 releases the rod 9, and the pistons 5 and 6 are abruptly displaced by the action of compression spring 8 upwardly in FIG. 3, until the piston 6 encounters the end of the hollow cylindrical section 3. In this manner the liquid inlet Z and the liquid outlet A are closed, on the one hand, and on the other hand the volume of the expansion chamber 4 increases until it has reached a maximum when pistons 5 and 6 are in the second position at the end of their displacement. This results in a great expansion of the liquid enclosed in the expansion chamber 4 and a release of the carbon dioxide contained in the liquid.

Furthermore, when the pistons 5 and 6 are in this position, the expansion chamber 4 is connected by passage 115 to the pressure gauge. The pressure can now be read on the pressure gauge 14.

When the measurement is completed, the pistons 5 and 6 are returned to the first position by means of the knob 10 and the rod 9 and the catch is engaged by the action of spring 13 and locks the piston in this first position.

The embodiment shown in FIG. 3 has the great advantage that the connection between the expansion chamber and the pressure gauge is not opened until the expansion chamber is shut off again from the feed line. In this manner the full line pressure cannot act on the pressure gauge. The pressure that builds up in the expansion chamber when the liquid flows into it is prevented from affecting the pressure gauge because, when the pistons are released, the pressure is relieved by the expansion of volume that takes place in the expansion chamber.

Figure 4:
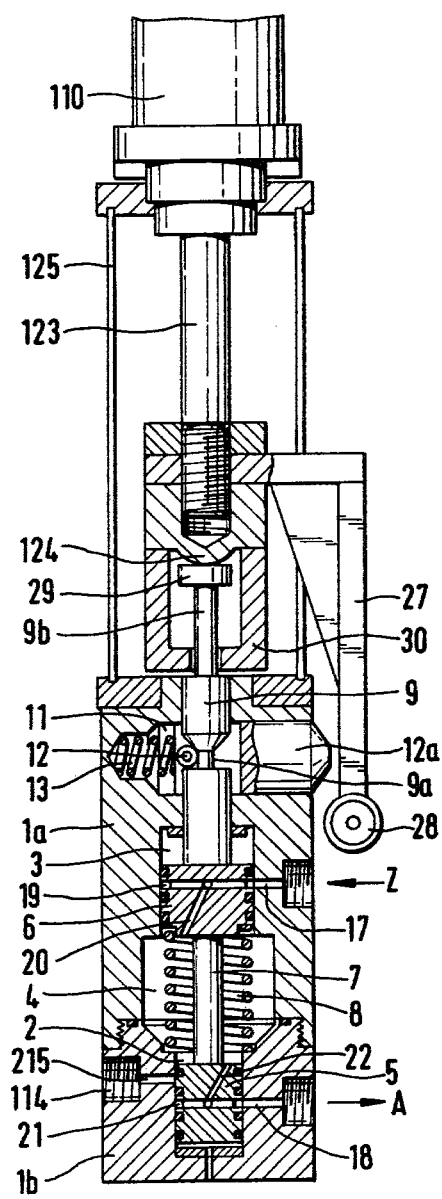
FIG. 4 is a side view, partially in cross section, of a second embodiment of an apparatus for determining the carbon dioxide content of a liquid.
Figure 5:
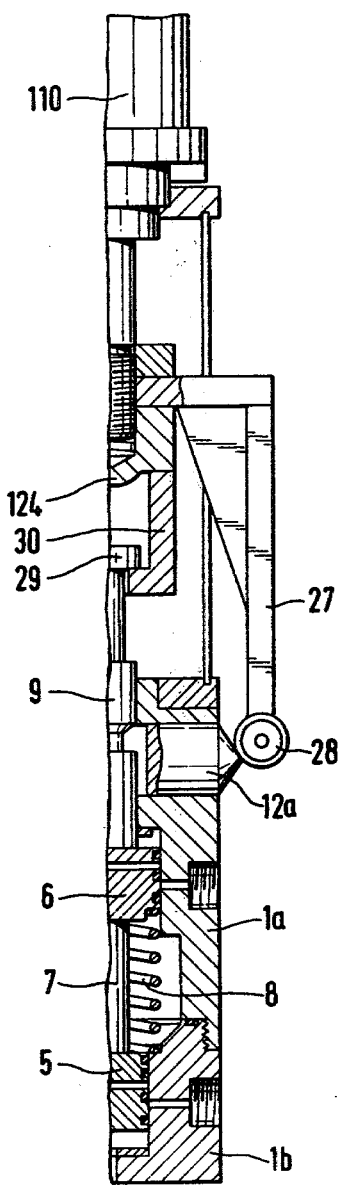
FIG. 5 is a representation similar to FIG. 4 of a half of the apparatus of FIG. 4 with the pistons in a different position.

In FIGS. 4 and 5 there is shown an embodiment of an apparatus for determining the carbon content of a liquid, which can be permanently installed on a pipeline or liquid container, and which is especially usable for measurement at relatively brief intervals of time.

The embodiment shown in FIGS. 4 and 5 is again basically the same in construction as the embodiment in FIG. 1, and again the same reference numbers are used for the same parts as in FIG. 1.

The embodiment in FIGS. 4 and 5 differs from that of FIG. 1 substantially in that the release of the catch means which brings about the displacement of the pistons 5 and 6 from the first position to the second position is accomplished automatically by an air cylinder rather than by hand. Likewise, the return of the pistons 5 and 6 to the first position is performed automatically by the air cylinder.

Since the internal construction of the embodiment in FIGS. 4 and 5 is the same as that of FIGS. 1 and 2, the above description of the latter may be consulted. In contradistinction to the embodiment in FIGS. 1 and 2, the embodiment shown in FIGS. 4 and 5 has no pressure gauge, but instead a pressure gauge, which is not shown and can be disposed at any other point, is connected to the terminal 114 and is thereby connected by passage 215 to the hollow cylindrical section 2. The groove 21 in piston 5 is so disposed that, when piston 5 is in the first position, in which the latter abuts against the end surface defining the hollow cylindrical section 2, it is opposite the passage 18 which is connected to the liquid outlet A. In this position, therefore, the expansion chamber 4 is connected to the liquid outlet A. When piston 5 is in the second position, in which piston 6 abuts against the end surface defining the hollow cylindrical section 3, the groove 21, however, is situated opposite passage 215 leading to connection 114. This means that, in this position, the pressure gauge is connected to the expansion chamber 4 through the connection 114, the passage 215, groove 21 and passage 22.

The entire apparatus is joined permanently to an air cylinder 110 by a mounting 125. The piston rod 123 of the air cylinder 110 is in line with or parallel with the rod 9 joined to the pistons 5 and 6. It has on its forward end an abutment 124 which is able to transmit thrust forces to a flange 29 which is disposed on the forward end 9b of the rod 9. Furthermore, the piston rod 123 is fixedly attached to an actuator 27 of offset construction which is guided parallel to the outside wall of the housing part 1a at a given distance therefrom. On the end of the actuator 27 pointing away from the air cylinder 110 and guided along the outside of the housing part 1a there is disposed an actuator roller 28. The arrangement is such that the actuator roller 28 is moved over the pushbutton 12a when a reciprocating movement of the actuator 27 takes place (see FIG. 5), thereby forcing it inwardly against the force of the spring 13.

On the piston rod 123 there is furthermore disposed a forwardly reaching claw 30 which encompasses with clearance the forward end 9b of the rod 9 and overreaches the flange 29. The length of the claw 30 is made such that between it and the flange 29 there remains sufficient clearance so that the pistons 5 and 6 can be displaced by the action of the compression spring 8 freely from the first to the second position when the catch means is released, but that on the other hand, when a complete displacement to the second position does not take place, the pistons 5 and 6 are positively carried to this position by the cooperation of the claw 30 with the flange 29.

The operation of the embodiment represented in FIGS. 4 and 5 is as follows:

In the previously-mentioned first position, the pistons are shifted downwardly as represented in FIG. 4. In this position the rod 9 is locked by the catch 12, so that the compression spring 8 exercises a force working upwardly in the drawing, but no displacement of the pistons can take place. In this first position the volume of the inner chamber of the housing is at a minimum, as already stated. Furthermore, the groove 19 in piston 6 is opposite the outlet end of the passage 17, while the groove 21 of piston 5 is opposite the outlet end of the passage 18. This means that liquid inlet Z and liquid outlet A are open in this position. The liquid to be measured can enter at Z and passes into the chamber 4, flows through it, and flows back out of the apparatus through the liquid outlet A. As soon as the liquid flows bubble-free through the expansion chamber, the catch is released by means of pushbutton 12a. To do this, the air cylinder 110 is operated such that the actuator 27, and with it the actuator roller 28, moves from the position represented in FIG. 5, through the position represented in FIG. 5, to an end position which is not shown. In this movement the actuator roller 28 rolls over the pushbutton 12a, which is briefly pushed inwardly. The ring 12 releases the rod 9 and the pistons 5 and 6 are abruptly driven upwardly in the drawing by the action of the compression spring 8, until the piston 6 abuts against the end wall of the hollow cylindrical section 3. Thus, the liquid inlet Z and the liquid outlet A are closed, on the one hand, and on the other hand the volume of the expansion chamber 4 increases until it has reached a maximum in the second position of the pistons 5 and 6 at the end of their movement. This brings about the already-described great expansion of the liquid enclosed and the release of the carbon dioxide contained in the liquid. Furthermore, in this position of the pistons 5 and 6, the expansion chamber is connected by the passage 215 to the connection 114 for the pressure gauge. By the piston displacement an additional volume is created in which a vacuum is formed. A state of equilibrium then establishes itself between the carbon dioxide content of the liquid and the gas pressure in the liquid-free chamber. The pressure can then be read on the pressure gauge attached to the connection 114. Furthermore, by means of the thermometer, which is no longer shown, the temperature of the liquid is determined. The carbon dioxide content of the liquid can be determined, as already stated, on the basis of the measured values.

After the measurements have been read, the air cylinder 110 is operated such that its piston rod 123, by means of the abutment 124 and the rod 9, pushes the pistons 5 and 6 back to the first, starting position. This movement takes place substantially more slowly than the movement from the first to the second position produced by the compression spring 8. The catch is engaged by the action of the spring 13 and holds the piston in the first position. The liquid inlet Z and the liquid outlet A are again open in this position and the apparatus is ready for a second measurement.

After the apparatus has lain idle for a relatively long period, it can happen that, when the catch has been released, the force of spring 8 is no longer sufficient to move pistons 5 and 6 to the second position in the desired rapid, abrupt manner, because the pistons, due to the swelling or sticking of its rings, is too greatly retarded. In this case, the claw 30 described above will positively carry pistons 5 and 6 to the second position. After a number of back-and-forth actuations of the apparatus the friction between the pistons 5 and 6 and the inner walls of the hollow cylindrical sections will have reduced to such an extent that the pistons will be brought by the force of spring 8 to the second position before the positive action begins.

It is desirable that the operation of the air cylinder 110 be performed within a given, favorable interval of time of a length such that, between the two movements, not only will a complete expansion of the liquid and release of the carbon dioxide contained in the liquid take place, but also the pressure that is established will be able to be read. And it may be desirable for a signal to appear—for example the lighting of a lamp—in a manner not actually shown, for example on the control device of the air cylinder or on the apparatus itself, which will indicate each time whether the pistons 5 and 6 are in the second position, i.e., which will indicate precisely the time interval within which a reading of the pressure can take place. The entire apparatus is then operated constantly in an intermittent manner, and the operator supervising the equipment can read the pressures at given intervals, having to wait no more than a few seconds each time until the signal appears which indicates when the gauges can be read.

In this embodiment, the pressure and temperature values can be read and detected automatically by special devices and fed to a central processing apparatus at the given intervals of time.

The embodiment described in FIGS. 4 and 5 has the great advantage that, by simplified constructional means, an automatically operating apparatus is obtained wherein the movement of the pistons from the first position to the second position and back from the second position to the first position takes place as in the case of a hand apparatus, that is, one in which the movement from the first position to the second takes place abruptly, while the return to the first position takes place much more slowly. It has been found in practice that this is the best kind of movement, since it permits a rapid and complete outgassing of the liquid by the expansion. The return of the pistons to the starting position, however, can be performed much more slowly.

Since in the embodiment shown in FIGS. 4 and 5 the operation of an apparatus operated by hand is imitated by the automatically operating apparatus, the additional advantage is obtained that the apparatus which is conceived as a hand instrument can be converted with little cost and trouble to a permanently installed apparatus operated by air cylinders.

The separation of the function of moving the pistons from the first position to the second position from that of their return to the first position additionally provides the advantage that the time occupied by the filling phase and the time occupied by the measuring phase of the overall measuring procedure can be of different length and can be predetermined. The adjustment can be made at the control means of the air cylinder.

The amount of liquid required for the measurement is small in all embodiments. The expansion chambers can be of such size that they have a capacity of from 15 to 60 cubic centimeters of liquid. In the case of a volume of approximately 35 cubic centimeters, allowing for the amount of liquid flowing through the expansion chamber before the measurement begins, approximately 200 cubic centimeters of liquid are required for each individual measurement.

The liquid losses, therefore, are extremely slight, even in the case of embodiments in which the liquid outlet is not connected back to a liquid-carrying line or to a liquid reservoir.

What is claimed is:

1. In an apparatus for determining the carbon dioxide content of a liquid, especially of a beverage, comprising a housing which has an expansion chamber for receiving the liquid to be measured, said chamber connected to an inlet line and an outlet line provided with valve means to a liquid inlet and a liquid outlet, respectively, and which is or can be connected to a pressure gauge and to a temperature measuring device, and whose volume is variable according to the position of a piston guided displaceably in it, and having a means for the displacement of the piston from a first position in which the volume of the expansion chamber is at a minimum to a second position in which the volume of the expansion chamber is at a maximum, the improvement wherein said apparatus comprises a plurality of hollow cylindrical sections comprising a first hollow cylindrical section and a second hollow cylindrical section each of which accommodates a displaceably guided piston, said pistons being in line with one another axially, and rigidly joined with one another, the piston of said first hollow cylindrical section being of a smaller diameter than the piston of said second hollow cylindrical section, said expansion chamber being disposed between the confronting end surfaces of said pistons and connected at one of its ends to a liquid feed line carried through the piston of said second hollow cyindrical section and at its other end to a liquid drain line carried through the piston of said first hollow cylindrical section, said pistons serving as valve means in that, in the first position of said piston, the liquid feed line and liquid drain line are open and upon movement of said pistons to a second position, said lines are closed, said apparatus comprising means for the displacement of said pistons from said first position to said second position.

2. Apparatus of claim 1 wherein in said housing a compression spring is disposed which exercises on the pistons a force in the direction of movement to the second position, and the piston of said second hollow cylindrical section is joined on its side facing the expansion chamber to a rod which is carried outwardly and which engages a catch means which holds said pistons in the first position, said catch means releasably connected to a pushbutton protruding from the outside of the housing.

3. Apparatus of claim 2 wherein said catch means has a groove disposed on the rod within said housing, which is engaged by a catch which is held by spring force in said groove and is connected to said pushbutton whereby it can be pressed out of the groove against the force of a spring for the release of the rod and hence of said pistons.

4. Apparatus of claim 2 wherein said rod has on its outer end a handle.

5. Apparatus of claim 4 constructed as a portable apparatus which can be connected to a liquid line or to a liquid container, the external form of the housing being substantially cylindrical and the pressure gauge being disposed on one end of the cylinder, while the handle is situated at the other end of the housing.

6. Apparatus of claim 2 wherein the outer end of said rod is coupled with a piston rod of an air cylinder by a thrust transmitting connection, said piston rod of said air cylinder being fixedly attached to an actuator which is displaceably guided longitudinally at a given distance from the housing and bears on its end an actuating roller which, upon a displacement of said actuator, moves at a given distance away, along a prescribed path along the outside of the housing, in which path said pushbutton is disposed.

7. Apparatus of claim 6 wherein on the outer end of said rod there is disposed a flange which is opposite an abutment disposed on the outer end of the piston rod of the air cylinder and on the outer end of the piston rod of the air cylinder there is disposed a claw reaching with clearance behind said flange.

8. Apparatus of claim 6 wherein the housing has on its circumferential surface a rotatable ring, a scale being provided on said ring and the adjacent portions of the outer wall of the housing for the reading of the carbon dioxide content in relation to pressure and temperature.

9. Apparatus of claim 2 wherein said compression spring is disposed in said expansion chamber and thrusts against the face of the piston of said second hollow cylindrical section.

10. Apparatus of claim 1 wherein a throttle member is disposed in said liquid outlet.

11. Apparatus of claim 1 wherein said liquid inlet and said liquid outlet are respectively connected by passages to the second and first hollow cylindrical sections respectively, the mouths of the passages in these sections being situated each in a position which, when the piston in question is in the position corresponding to the volume minimum of said expansion chamber, is opposite an aperture in the piston which is connected to said expansion chamber by a connecting passage running through the piston .

12. Apparatus of claim 1 wherein a pressure gauge is connected by a passage to at least one of said hollow cylindrical sections of the inner chamber of the housing, the entry of the passage into this section taking place at a point which, in the second position of the particular piston corresponding to the maximum volume of the associated expansion chamber, is opposite an aperture in the piston of the first hollow cylindrical section which is connected to said expansion chamber by a connecting passage running through the piston of said first hollow cylindrical section.

13. Apparatus of claim 12 wherein said expansion chamber is connected to said liquid outlet or to the liquid inlet, as the case may be, when the piston of said first hollow cylindrical section is in the first position corresponding to the minimum volume of said expansion chamber and, when the piston of said first hollow cylindrical section is in the second position corresponding to the maximum volume of said expansion chamber, it is connected to said pressure gauge.

14. Apparatus of claim 1 wherein a temperature measuring means is disposed such that its probe is situated in said expansion chamber in the immediate vicinity of the entry orifice of said liquid feed line.

15. Apparatus of claim 1 wherein the volume of said expansion chamber amounts to a minimum of 15 to 60 cm$^3$.

16. Apparatus of claim 1 wherein said housing consists, at least in the area of said expansion chamber, of transparent material.

17. Apparatus of claim 1 fixedly disposed on a liquid container or in the bypass of a liquid line, connections being disposed on the housing for the carbon dioxide pressure gauge and the temperature measuring means, which are connected to a central processing system.

* * * * *

UNITED STATES PATENT AND TRADEMARK OFFICE
CERTIFICATE OF CORRECTION

PATENT NO. : 4,276,769

DATED : Jul. 7, 1981

INVENTOR(S) : Dieter Wieland et al

It is certified that error appears in the above–identified patent and that said Letters Patent are hereby corrected as shown below:

Title Page Assignee    Insert --Assignee: Firma Fuellpack Dipl. -Brauerei - Ingenieur Dieter Wieland, Dusseldorf, Germany--.

Signed and Sealed this

Nineteenth Day of January 1982

[SEAL]

Attest:

GERALD J. MOSSINGHOFF

Attesting Officer    Commissioner of Patents and Trademarks